United States Patent [19]
Holt

[11] Patent Number: 5,869,533
[45] Date of Patent: Feb. 9, 1999

[54] NON-IRRITATING CAPSAICIN FORMULATIONS AND APPLICATORS THEREFOR

[76] Inventor: Stephen D. Holt, 60 Tallyho, Little Rock, Ark. 72227

[21] Appl. No.: 106,834

[22] Filed: Jun. 30, 1998

Related U.S. Application Data

[63] Continuation-in-part of Ser. No. 635,149, Apr. 23, 1996.

[51] Int. Cl.$^6$ .................................................... A61K 31/16

[52] U.S. Cl. .......................... 514/627; 424/77; 424/78.05; 424/195.1; 514/825

[58] Field of Search ..................................... 514/627, 825; 424/77, 78.05, 195.1

[56] References Cited

U.S. PATENT DOCUMENTS

| | | | |
|---|---|---|---|
| 4,546,112 | 10/1985 | LaHann et al. | 514/627 |
| 4,681,897 | 7/1987 | Brand | 514/557 |
| 4,939,149 | 7/1990 | Blumberg et al. | 514/691 |
| 5,599,342 | 2/1997 | LaHann | 514/282 |
| 5,756,107 | 5/1998 | Hahn et al. | 424/401 |

*Primary Examiner*—Keith D. MacMillan
*Attorney, Agent, or Firm*—Wendy Buskop; Chamberlain, Hrdlicka et al.

[57] ABSTRACT

A delivery system for applying a formula containing capsaicin together with another ingredient to neutralize the discomfort resulting from the application of capsaicin to the skin which involves the topical application of capsaicin by use of patches, use of second skin, use of sprays and includes a unique method for applying the formulation using laser on the epidermis.

31 Claims, No Drawings

NON-IRRITATING CAPSAICIN FORMULATIONS AND APPLICATORS THEREFOR

RELATED APPLICATIONS

This is a continuation-in-part application of co-pending U.S. patent application Ser. No. 08/635,149 that was filed on Apr. 23, 1996.

BACKGROUND OF THE INVENTION

In one aspect, this invention relates to a novel applicator method for a unique composition of matter which is the subject of a copending patent application that is useful for treating bodily pains and discomforts. In one aspect, this invention relates to a method for treating bodily pains and discomforts. In yet another aspect, this invention relates to formulating a pain and discomfort reliever.

Arthritis is medically termed as an inflammation of a joint or joints and is one of a number of diseases and disorders of the skeleton and body system. Arthritis arises from many causes, some well-defined, some still unknown, and it is treated in many different ways. There are two common types, the first of which is inflammatory, of which rheumatoid arthritis is the most commonly acknowledged and a non-inflammatory, second type, most commonly represented by degenerative joint disease, or "wear and tear" arthritis. Inflammatory arthritis is a disease not of the joints alone but of the whole bodily system, in particular, the connective tissues of the body. It is an autoimmune disease, where the body's immune system attacks its own host (i.e. itself) and produces inflammation. Degenerative joint disease is a chronic joint disease, often occurring in more elderly people. In both cases many manifestations are similar. The joints, whether singly or in multiples, are affected. The joints may become swollen, warm, deformed, gnarled, and in many instances present grotesque deformities. In many cases it also affects the adjacent muscles and tendons, as well as other connective tissues of the body. The primary disease produces symptomatic swelling, pain and stiffness.

Various new and old drugs have been developed for the treatment of arthritis, anywhere from non-steroidal anti-inflammatory drugs to cortisone. Many of these systemic drugs have dangerous side effects. Their dosage must be carefully prescribed and administered under controlled conditions and circumstances to avoid unpleasant and dangerous side effects.

Several topical agents (creams, ointments, liniments and the like) have been utilized for the relief of the pains and aches of arthritis and related disorders. Most of these have provided a little, but only temporary, relief to persons suffering from pain. Many combinations of varying ointments, creams, aqueous solutions, liniments and the like for the treatment of arthritis are known. The most efficacious of these contains as its active ingredient the vegetable products derived from the seed and pods of the capsicum plant, commonly known as red pepper. Capsicum-derived topical agents are devised for external application to the affected area of the body by applying to the area adjacent to the muscle, joint, ligament or tendon and then rubbing it into the skin. The active ingredient is capsaicin. With initial as well as continuous use, capsaicin is effective to relieve the aches and pains of various musculo-skeletal disorders, such as arthritis, muscle strains, sprains, tendinitis, bursitis and other soft tissue diseases.

Capsaicin is also effective to relieve the various musculoskeletal pains, itching, neuropathic pains, dysesthesias caused by shingles, post herpetic neuralgia, post mastectomy pain, and peripheral neuropathies. It is further commonly prescribed to reduce the pain of neuropathies produced by diabetes (burning pain, discomfort, often at night) and other diseases that are neuropathic in origin including the discomfort and odd sensations of shingles (post herpetic neuralgia, which can be extremely painful), as well as dysesthesias that can occur with thoracotomies and post surgical scars.

Unfortunately, although capsaicin is often the most effective agent available, the active ingredient is a potent skin irritant, producing a burning, uncomfortable sensation to the skin. Although prescribed frequently, it is used to only a limited extent due to this unpleasant side effect.

The burning side effect has also discouraged the use of capsaicin to treat other types of discomfort, such as pruritus or itching. Pruritus or itching can be caused by many stimuli, such as poison ivy, hemorrhoids, or athlete's foot. The unpleasant side effects of capsaicin have discouraged its use to treat such types of discomfort.

A capsaicin based pain reliever which does not irritate the skin or cause a burning discomfort would be extremely desirable and acceptable to patients and people in general who are experiencing the types of pain or discomfort outlined above.

The present invention relates to different types of applicators usable with a unique capsaicin based formula. The applicators and methods for applying include the use of polymeric based patches, the use of topical second skin applications, the use of sprays, sticks, wicked liquids, rollons and methods of application which include the use of a laser to remove the first layer of the epidermis, and thus allowing application of the patch to allow a more rapid absorption.

OBJECTS OF THE INVENTION

It is an object of this invention to provide a capsaicin based pain reliever application which can be easily removed and reapplied to human skin.

It is another object of this invention to provide a method for applying the capsaicin-based pain reliever formula using a patch and laser system which involves the removal of the top layer of epidermis.

Another object of the invention is to provide for different types of applicators, such as aerosol, wicked liquid, spray, topical second skin, roll-on such that the formulation can be adhered to the skin using other mechanical devices instead of the human hand..

SUMMARY OF THE INVENTION

In accordance with one aspect of the invention, there is provided a polymeric base with removable adhesive usable on human skin further containing a pre-loaded supply of a composition comprising a first active ingredient and at least one second active ingredient in a carrier fluid. The first active ingredient comprises capsaicin. The at least one second active ingredient is to reduce the sensation of capsaicin induced skin irritation.

In accordance with another aspect of the invention, there is provided a method for treating a victim of pain or discomfort with a patch wherein the patch is applied topically to the skin of the victim near an area affected by the pain or discomfort, using the unique capsaicin formula, and then lasers are used to remove the first layer of skin and the patch, relieving the pain of arthritis.

In accordance with a further aspect of the invention, there is provided a method for making a patch using a composition useful for topical application to treat pain or discomfort. The method is carried out by first mixing a carrier with at least one first active ingredient comprising capsaicin and at least one second active ingredient to reduce capsaicin induced skin irritation to form an aqueous or oil-based solution, or a solid stick applicator or patch, of the at least one first active ingredient and the at least one second active ingredient in the carrier. The aqueous solution may have a cream-like viscosity, or can be wax-like and applied to a polymeric base which can then be applied to the skin.

DETAILED DESCRIPTION OF THE PREFERRED EMBODIMENTS

Capsaicin is trans-8-methyl-N-vanillyl-5 nonenamide, a naturally occurring alkyl vanillylamide, a type of capsaicinoid. It is found in high concentration in fruit of plants of the Capsicum genus. The chili pepper, red pepper and paprika are all species of Capsicum. Capsicum is the dry powder obtained by grinding up the fruits of these plants. Capsicum oleoresin (or capsaicin oleoresin) is the liquid concentrate extracted from the dry powder. Capsaicin, a white crystalline material, is obtained from the liquid concentrate.

The composition of the invention comprises capsaicin as a first active ingredient and at least one second active ingredient is to reduce the sensation of capsaicin induced skin irritation. The ingredients are contained in a carrier.

Generally speaking, the composition will contain in the range of 0.00125% to 1% by weight of capsaicin. However, compositions containing less than 0.00125% by weight of capsaicin will provide a diminishing, but still therapeutic, effect. Even trace concentrations of capsaicin (such as 0.00001% by weight) will provide a minute therapeutic effect. Compositions containing more than 1% by weight of capsaicin will also provide a therapeutic effect, except that the burning side effect will increase in proportion to the increase percentage of capsaicin. Compositions containing 5%, or more, by weight of capsaicin could be used, but the burning sensation is considered intense. For these reasons, compositions containing in the range of 0.025% to 0.25% by weight of capsaicin are preferred because they are narrowly encompassed within current FDA guidelines. However, the FDA guidelines were developed at a time when there was not an effective method for relieving the discomfort generated by capsaicin. The present invention increases the amount of capsaicin that can be administered comfortably. Generally speaking, a sufficient amount of the at least one second active ingredient is mixed with the carrier to reduce the skin irritation and pain which is caused by the capsaicin.

Preferably, a fluid carrier is water-based and forms an aqueous solution containing the ingredients. An oil-based carrier solution containing the ingredients is an alternative to the aqueous carrier solution. Either aqueous or oil-based solutions further contain thickening agents to provide the composition with the viscosity of a liniment, cream, ointment, gel, or the like. Suitable thickening agents are well known, to enable the patch to be applied to human skin. The composition can be mixed with "second skin" or "liquid skin" carriers so that the composition is rigorously adhered to the skin without the need for the polymeric applicator. Other carriers, such as paraffin or wax can also be mixed with the composition. so that it can be rolled on, wicked onto the skin or applied like a stick onto the skin. Alternatively, aerosols can be used, with propane propellants to disperse the composition containing capsaicin into the skin in a thin, even mist for light application.

Alternative embodiments of the present invention can also use a solid devices containing the active ingredients, wherein the active ingredients are squeezed out of the device, made from plastic or the like.. This enables the alternative embodiment to be applied via the familiar stick applicator. The solid carrier further contains thickening agents to provide the composition with the consistency of wax or paraffin.

The at least one second active ingredient can be of various functionalities. The second active ingredient can be selected from the group consisting of at least one binding agent for binding capsaicin and at least one topical analgesic agent for analgesthetizing against pain caused by the effects of capsaicin.

It is preferred that the second active ingredient comprise a plant extract. For example, a selection from the group consisting of a nettle extract, a yarrow extract, a horsetail extract, a birch extract, a rosemary extract, a horsetail extract, a ginger extract, a chamomile extract, a birch extract, a lavender extract, a bergamot extract, a coltsfoot extract and comfrey extract is expected to be beneficial.

In the preferred embodiment of the specific end use of the novel composition, a removable patch is envisioned for applying an arthritis cream which comprises a polymeric base. The arthritis cream applied to the polymeric base comprises a first active ingredient comprising capsaicin and at least one second active ingredient that functions as an analgesic to reduce capsaicin induced skin irritation; and an adhesive for adhering the polymeric base to human skin is also used to hold the patch onto the skin. It is preferred to use a water resistance polymeric base.

In the a preferred embodiment, the removable patch uses capsaicin in the range of 0.0001% to 0.025% by weight of capsaicin, although in the most preferred embodiment, the capsaicin used is in the range of 0.025% to 0.25% by weight of capsaicin.

Carriers contemplated within the scope of the invention can be oil based, aqueous or even further contain additives such as a thickening agent to improve the consistency of the composition such as liniment, cream, gel, ointment or mixtures thereof. Binding agents could also be added to the composition.

Ingredients to improve the smell of the pepper based formula are also considered within the scope of the invention. These ingredients are useful in the roll on and aerosol versions of the present invention. They include one or more ingredient such as polyol, a nettle extract, a yarrow extract, a horsetail extract, a birch extract, a rosemary extract, a horsetail extract, a ginger extract, a chamomile extract, a birch extract, a lavender extract, a bergamot extract, a coltsfoot extract and a comfrey extract or mixtures thereof.

The polyol can be a propylene glycol, glycerine, polyethylene glycol, butylene glycol, triethanolamine and mixtures thereof.

While the preferred embodiment of the present invention includes all of the above-mentioned extracts, individual extracts can be excluded to achieve diminished, though therapeutic, results. The order of effectiveness of the various extracts is listed below:

1. lavender extract
2. bergamot extract
3. rosemary extract
4. ginger extract
5. chamomile extract
6. birch extract
7. horsetail extract 8. nettle extract
9. yarro extract
10. coltsfoot extract
11. comfrey extract The concentrations of the various extracts can be varied or eliminated to achieve enhanced or diminished effectiveness of the alternate second active ingredients.

Nettle extract can be obtained from the leaves of *Urtica dioca*. It is a medium green-yellow liquid which is soluble in water, has a characteristic odor, a specific gravity in the range of 1.02 to 1.05 at 25 degrees C., a pH in the range of 4.0 to 7.0 at 25 degrees C., and a refractive index in the range of 1.3860 to 1.3950 at 25 degrees C.

Yarrow extract can be obtained from the flowers of *Achillea millefolium*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Horsetail extract can be obtained from the leaves of *Tussilago farfara*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Birch extract can be obtained from the leaves of *Betula alba*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Rosemary extract can be obtained from the leaves of *Rosmarinus officinalls*. It is a light to medium amber liquid which is soluble in water, has a characteristic odor, a specific gravity in the range of 1.02 to 1.05 at 25 degrees C., a pH in the range of 4.0 to 5.5 at 25 degrees C., and a refractive index in the range of 1.3860 to 1.3950 at 25 degrees C.

Horsetail extract can be obtained from the whole plant of *Equiseturn hyemale*. It is a light to medium amber liquid which is soluble in water, has a characteristic odor, a specific gravity in the range of 1.02 to 1.05 at 25 degrees C., a pH in the range of 4.0 to 5.5 at 25 degrees C., and a refractive index in the range of 1.3860 to 1.3950 at 25 degrees C.

Ginger extract can be obtained from the roots of *Zingiber officinale*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Chamomile extract can be obtained from the flowers of *Matricaria chamomilla*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Birch extract can be obtained from the leaves of *Symphyturn officinale*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Lavender extract can be obtained from the flowers of *Lavandula officinalis*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

Bergamot extract can be obtained from the flowers of *Monarda didyma*. It is a light to medium amber liquid which is soluble in water, has a characteristic odor, a specific gravity in the range of 1.02 to 1.05 at 25 degrees C., a pH in the range of 4.0 to 6.5 at 25 degrees C., and a refractive index in the range of 1.3860 to 1.3950 at 25 degrees C.

The plant extracts can be used in the form of propylene glycol-water solutions of the indicated materials.

The composition of the invention will often also contain a polyol such as a polyol selected from the group consisting of propylene glycol, glycerine, polyethylene glycol, butylene glycol, and triethanolamine. Other ingredients such as inositol, methyl paraben, propyl paraben, carbomer 940 and DL-panthenol may be present if desired.

In the method of the invention, a victim of pain or discomfort is treated by applying the above described composition topically to the skin of the victim near an area affected by the pain or discomfort. The types of pain or discomfort to which the invention may be applied include those discussed in the background of the invention. Generally speaking, the inventive composition, preferably in ointment or cream form, is applied to the selected area, such as a joint, and rubbed in. The amount applied is not critical. Generally, it should be applied in an amount which is sufficient to wet the area of application. Usually, the amount used will be in the range of from about 0.3 to about 3 ccs.

For the treatment of pruritus or itching, the application of the composition can be repeated as required to control the discomfort. When the preferred composition of the invention is applied, it provides near immediate relief from the itching caused by poison ivy or hemorrhoids, without a burning sensation. The relief lasts for several hours. It is surprising that a capsaicin based composition would be useful for the treatment of such discomfort. Capsaicin, as part of the present invention, has been shown to be effective in relieving: 1) musculo-skeletal pains (e.g., arthritis, tendinitis, bursitis, myalgias, arthralgias, strains, sprains, ligamentous disorders, etc.); 2) peripheral neuropathy and other dysesthesias (e.g., diabetic peripheral neuropathy with burning numb feet); 3) post herpetic neuralgia (painful syndrome after shingles and other viral illnesses); 4) post mastectomy/post thoracotomy scar pain; and 5) pruritus and itching of all forms, whether contact dermatitis (e.g., poison ivy), immunological (e.g., angioedema that occurs with systemic lupus erythematosus or urticaria that occurs with various allergic reactions), drug reactions (e.g., sulfa, penicillin, etc.), insect bites, systemic metabolic disorders (e.g., pruritus that occurs with renal dialysis), mechanical maceration (e.g., hemorrhoids) and idiopathic pruritus.

For best results in the treatment of arthritis, the treatment should be repeated several times per day, such as in the range of 2 to 8 times per day, preferably 3–5 times per day, and continued for several days. Surprisingly, most patients do not experience the burning discomfort heretofore known as a very common side effect of topical capsaicin application.

In another method of use of the present invention, a superficial laser is used which removes the superficial epidermis in a non-painful manner. It does not leave scarrin after the laser treatment, the composition, such as by patch or spray is applied to the treated skin the composition is then absorbed into the blood stream so that the body rapidly absorbs the impact of the formula.

The foregoing is a description of the composition and method of use of an embodiment of the invention. The scope of the invention is considered to include the described embodiment together with others obvious to those skilled in the art.

EXAMPLE

A composition made in accordance with one embodiment of the invention contains the following ingredients.

| Ingredient | wt. % |
|---|---|
| deionized water | 81.00 |
| propylene glycol | 5.00 |
| glycerine | 3.00 |
| polyethylene glycol | 1.00 |
| butylene glycol | 1.00 |
| triethanolamine | .60 |
| inositol | .20 |
| methyl paraben | .10 |
| propyl paraben | .10 |
| carbomer 940 | .30 |
| DL-Panthenol | 1.00 |
| nettle extract | .50 |
| yarrow extract | .50 |
| horsetail extract | .50 |
| birch extract | .50 |
| rosemary extract | .50 |
| horsetail extract | .50 |
| ginger extract | .50 |
| chamomile extract | .50 |
| birch extract | .50 |
| lavender extract | .50 |
| bergamot extract | .50 |
| capsaicin | .025 |
| coltsfoot extract | .50 |
| comfrey extract | .50 |

What is claimed is:

1. A removable patch for applying an arthritis cream comprising:
   a polymeric base;
   a composition applied to the polymeric base comprising a first active ingredient comprising capsaicin and at least one second active ingredient that functions as an analgesic to reduce capsaicin induced skin irritation, wherein said at least one second active ingredient is selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof; and
   an adhesive for adhering the polymeric base to human skin.

2. The removable patch as in claim 1 wherein the composition further comprises capsaicin in the range of 0.0001% to 0.025% by weight of capsaicin.

3. The removable patch as in claim 1 wherein the composition further comprises capsaicin in the range of 0.025% to 0.25% by weight of capsaicin.

4. The removable patch as in claim 3 wherein the composition further comprises an aqueous fluid carrier.

5. The removable patch as in claim 4 wherein the composition further comprises a thickening agent to improve the consistency of the composition, wherein the thickener is selected from the group consisting of liniment, cream, gel, and ointment.

6. The removable patch as in claim 5 further comprises at least one binding agent for binding capsaicin to a second active ingredient.

7. The removable patch as in claim 3 wherein the polyol is selected from the group consisting of propylene glycol, glycerine, polyethylene glycol, butylene glycol, triethanolamine and mixtures thereof.

8. A method for treating a victim of a joint discomfort utilizing a patch comprising a self-adhering polymeric base, a composition disposed on the polymeric base consisting of a carrier fluid, at least one first active ingredient comprising capsaicin, and at least one second active ingredient that functions as an analgesic ingredient to reduce capsaicin induced skin irritation topically to the skin of the victim near an area affected by the discomfort wherein said at least one second active ingredient is selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof.

9. The method as in claim 8 wherein the composition disposed on the polymeric base further comprises at least one second active ingredient selected from the group consisting of at least one binding agent, and at least one topical analgesic agent for analgesthetizing against pain caused by the effects of capsaicin wherein said at least one second active ingredient is selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof.

10. The method as in claim 9 wherein the composition contains capsaicin in the range of 0.00125% to 1% by weight.

11. The method as in claim 9 wherein the composition contains capsaicin in the range of 0.025% to 0.25% by weight and the minimum amount of the at least one second active ingredient which is effective to reduce the skin irritation and pain which is caused by the capsaicin.

12. The method as in claim 8 wherein the composition further comprises an oil-based solution of the at least one first active ingredient comprising capsaicin and the at least one second active ingredient in the carrier.

13. A method for making a composition useful for topical application to treat a discomfort, said method comprising mixing a carrier with at least one first active ingredient comprising capsaicin and at least one second active ingredient to reduce capsaicin induced skin irritation to form an aqueous solution containing in the range of 5 to 99.5 percent by weight of capsaicin, wherein the second active ingredient forms an analgesic and is selected from the group consisting of a nettle extract, a yarrow extract, a horsetail extract, a birch extract, a rosemary extract, a horsetail extract, a ginger extract, a chamomile extract, a birch extract, a lavender extract, and a bergamot extract.

14. The method of claim 13 wherein the carrier is an oil-based fluid.

15. The method of claim 13 further comprising a thickening agent to provide the composition with the consistency selected from the group consisting of liniment, cream, gel, and ointment.

16. The method as in claim 15 wherein the carrier is in the form of a stick.

17. The method as in claim 16 further comprising a thickening agent selected from the group consisting of wax and paraffin.

18. A topical second skin preparation comprising a first active ingredient comprising capsaicin and at least one second active ingredient that functions as an analgesic to reduce capsaicin induced skin irritation selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof, and an adhesive for adhering non-toxically to human skin.

19. The topical second skin preparation as in claim 18 wherein the composition further comprises capsaicin in the range of 0.0001% to 0.025% by weight of capsaicin.

20. The topical second skin preparation as in claim 18 wherein the composition further comprises capsaicin in the range of 0.025% to 0.25% by weight of capsaicin.

21. The topical second skin preparation as in claim 18 wherein the composition further comprises a an aqueous fluid carrier.

22. The topical second skin preparation as in claim 18 wherein the composition further comprises a thickening agent to improve the consistency of the composition, wherein the thickener is selected from the group consisting of liniment, cream, gel, and ointment.

23. The topical second skin preparation as in claim 18 further comprises at least one binding agent for binding capsaicin to a second active ingredient.

24. The topical second skin preparation as in claim 18 wherein the polyol is selected from the group consisting of propylene glycol, glycerine, polyethylene glycol, butylene glycol, triethanolamine and mixtures thereof.

25. The topical second skin preparation as in claim 18 wherein the carrier of the preparation is selected from the group of carriers consisting of spray, bandaid or liquid skin.

26. A spray for treating an arthritis condition comprising a composition containing capsaicin in the range of 0.0001% to 0.25% by weight, an aerosol carrier, a binding agent, and a first active ingredient selected from the group consisting of 0.025% to 0.25% by weight of capsaicin and wherein the composition further comprises at least one second active ingredient selected from the group consisting of a polyol, a nettle extract, a yarrow extract, a horsetail extract, a birch extract, a rosemary extract, a horsetail extract, a ginger extract, a chamomile extract, a birch extract, a lavender extract, a bergamot extract, or mixtures thereof.

27. A method for treating arthritis comprising:
using a laser to remove the superficial epidermis of the body, treating the effected epidermis with an arthritis composition that has a first active ingredient comprising capsaicin and at least one second active ingredient that functions as an analgesic to reduce capsaicin induced skin irritation, wherein said at least one second active ingredient is selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof.

28. A method to stop itching on skin using a formula which comprises a first active ingredient comprising capsaicin, and at least one second active ingredient that functions as an analgesic to reduce capsaicin induced skin irritation, wherein said at least one second active ingredient is selected from the group consisting of a polyol, a nettle extract, a yarrow extract, a horsetail extract, a birch extract, a rosemary extract, a horsetail extract, a ginger extract, a chamomile extract, a lavender extract, a bergamot extract, a coltsfoot extract and a comfrey extract or mixtures thereof.

29. The method as in claim 28 wherein the composition further comprises capsaicin in the range of 0.0001% to 0.025% by weight of capsaicin.

30. The method in claim 28 wherein the composition further comprises a thickening agent to improve the consistency of the composition, wherein the thickener is selected from the group consisting of liniment, cream, gel, and ointment.

31. The method as in claim 28 wherein the polyol is selected from the group consisting of propylene glycol, glycerine, polyethylene glycol, butylene glycol, triethanolamine and mixtures thereof.

* * * * *